United States Patent [19]

Browne

[11] 4,296,115

[45] Oct. 20, 1981

[54] PYRIDYLALKYLAMINES

[75] Inventor: Leslie J. Browne, Morristown, N.J.

[73] Assignee: Ciba-Geigy Corporation, Ardsley, N.Y.

[21] Appl. No.: 145,533

[22] Filed: May 1, 1980

[51] Int. Cl.³ .................. C07D 213/36; A61K 31/44
[52] U.S. Cl. ..................................... 424/263; 546/300
[58] Field of Search ....................... 546/300; 424/263

[56] References Cited

U.S. PATENT DOCUMENTS 3,410,861 11/1968 McCloskey ........................ 546/329
3,952,101 4/1976 Yu-Wen Jen et al. ............. 546/300
4,260,619 4/1981 Mizzoni ............................... 424/263

OTHER PUBLICATIONS

Lezina et al., Chem. Abstracts, vol. 63, (10), 13,049h Nov. 8, 1965.

Dyumaev et al., Chem. Abstracts, vol. 63, (10), 13,049-h-13050a Nov. 8, 1965.

Smirnov et al., Chem. Abstracts, vol. 64(4), 5038c–e, Feb. 14, 1966.

Klingsberg, "Pyridine and Derivatives," Part Three, pp. 615–619, 643–646 and 772–777, Interscience Pub. (1962).

Primary Examiner—Alan L. Rotman
Attorney, Agent, or Firm—Norbert Gruenfeld

[57] ABSTRACT

Secondary hydroxypyridylalkylamines, e.g., those of the formula

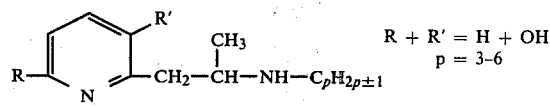

$R + R' = H + OH$
$p = 3-6$ and acid addition salts thereof are cardioprotective, e.g., antiischemic agents.

8 Claims, No Drawings

PYRIDYLALKYLAMINES

BACKGROUND OF THE INVENTION

According to U.S. Pat. No. 3,952,101, "α-aminomethyl-5-hydroxy-2-pyridinemethanols . . . have direct bronchodilator action with minimal cardiac stimulation," i.e., they have "greater activity on respiratory smooth muscle than on cardiac muscle."

Surprisingly, isomeric des-hydroxy analogs thereof, lacking the methanolic function, exhibit mainly cardioprotective effects with negligible bronchodilator action.

SUMMARY OF THE INVENTION

The present invention concerns and has for its object the provision of new secondary hydroxypyridylalkylamines, more particularly of those of Formula I

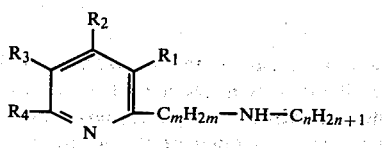

wherein one of $R_1$, $R_2$ and $R_4$ is hydroxy, and the others, as well as $R_3$, are hydrogen or lower alkyl; m is an integer from 2 to 4; and n is an integer from 1 to 7; or of acid addition salts thereof; of corresponding pharmaceutical compositions and of methods for the preparation and application of these products, which are useful cardioprotective, especially antianginal agents.

DESCRIPTION OF THE PREFERRED EMBODIMENTS

The hydroxy group $R_1$, $R_2$ or $R_4$ occupies any of the 3-, 4- or 6-pyridine-positions, but preferably one of $R_1$ and $R_4$ is hydroxy and the other, as well as $R_2$ and $R_3$ are advantageously hydrogen, lower alkyl, especially methyl, but also ethyl, n- or i-propyl or -butyl.

The alkylene group $C_mH_{2m}$ represents preferably 1,2-propylene, but also ethylene, 1,3-propylene, 1,2-, 1,3- or 1,4-butylene.

The lower aliphatic group $C_nH_{2n+1}$ is preferably lower alkyl, e.g., methyl, ethyl, n- or i-propyl, n-, i- or t-(butyl, pentyl, hexyl or heptyl); especially i-propyl.

Said group $C_nH_{2n-1}$ represents either lower alkenyl, e.g., allyl, methallyl, 2- or 3-(butenyl, pentenyl, hexenyl or heptenyl); or lower cycloalkyl, e.g., cyclopropyl, cyclobutyl, cyclopentyl, cyclohexyl or cycloheptyl; especially cyclopropyl or cyclohexyl.

The acid addition salts of the dibasic compounds of Formula I are preferably derived from the pharmaceutically acceptable acids listed below.

The compounds of the invention exhibit valuable pharmacological effects, for example, antihypertensive, but especially cardioprotective, e.g., antiischemic (i.e., antianginal) properties. This can be demonstrated in animal tests, using preferably mammals, such as rats, cats and dogs, or isolated organs thereof. Said compounds can be administered to them enterally or parenterally, advantageously orally or intravenously, for example within gelatin capsules or in the form of starchy suspensions or aqueous solutions respectively. The applied dosage may range between about 1 and 200 mg/kg/day, preferably between about 3 and 30 mg/kg/day i.v. or between about 10 and 100 mg/kg/day p.o.

Slight antihypertensive effects can be observed in spontaneous hypertensive rats or renal hypertensive dogs, either by sphygmomanometry at the rats' tail, or directly by means of a catheter placed into the dogs' femoral artery and a transducer; whereby the blood pressure is expressed in mm Hg.

The cardioprotective activity of said compounds is similar to that of nitroglycerin, propranolol and/or verapamil, which attenuate the electrocardiographic (ECG) manifestation (ST-T elevation) of myocardial ischemia produced by temporary coronary occlusion in anesthetized cats or conscious dogs. The latter were subjected to a left thoracotomy under pentobarbital anesthesia and artificial respiration. The pericardium was opened and a segment of the left coronary artery was exposed to allow the implantation of a silastic balloon occluder around it, which was exteriorized through the back of the neck at the shoulder blade and a protective jacket was fitted. The dogs were allowed to recover for 7 to 10 days and antibiotics are given the first four days after surgery. The dogs are then subjected to a priming occlusion during which no ECG-readings are taken. Thereupon 2 to 3 occlusions of 1–1.5 minutes duration are conducted in 5 minute intervals and the change in ST-T segment of the lead II ECG is recorded and averaged before and at designated intervals after drug treatment, and the results are expressed as ratio of treated and untreated (control) response. Also permanent coronary occlusion is performed, venous blood samples are drawn for CPK-determinations 3, 6 and 24 hours after occlusion, whereupon the dogs are anesthetized, injected with Trypan blue dye, sacrificed with an overdose of sodium pentobarbital and the hearts dissected to estimate the necrotic tissue. According to the results obtained, the compounds of the invention significantly reduce the electrical, enzymatic and morphological changes (infarct size) caused by coronary occlusion in conscious dogs. Therefore, they are useful cardioprotective, especially antianginal agents. Moreover, said compounds are also valuable intermediates in the production of other useful products, especially of pharmacologically active compositions.

Particularly useful are compounds of Formula I, wherein one of $R_1$, $R_2$ and $R_4$ is hydroxy, and the others, as well as $R_3$, are hydrogen or methyl, m is the integer 2 or 3 and n is an integer from 2 to 6, or a pharmaceutically acceptable acid addition salt thereof.

Preferred compounds of this invention are those of Formula II

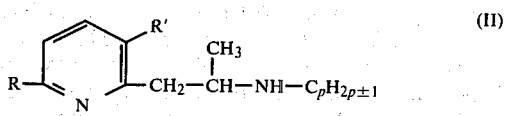

wherein one of R and R' is hydroxy and the other is hydrogen, and p is an integer from 3 to 6, or a pharmaceutically acceptable acid addition salt thereof.

Outstanding are those compounds of Formula II, wherein $C_pH_{2p\pm1}$ represents i-propyl, t-butyl, allyl or cyclopropyl, or a pharmaceutically acceptable acid addition salt thereof.

The compounds of this invention are prepared according to conventional methods, for example by:

(a) hydrolyzing a compound of Formula III

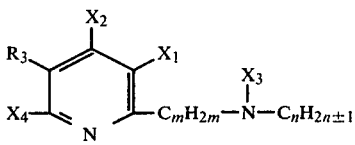

(III)

wherein one of $X_1$, $X_2$ and $X_4$ is hydroxy substituted with an alkali metal, the monohalide of an alkaline earth metal, or the acyl radical of an aliphatic or aromatic carboxylic or sulfonic acid, and the others are hydrogen or lower alkyl; $X_3$ is hydrogen, an alkali metal, the monohalide of an alkaline earth metal or said acyl radical, and the other symbols have the meaning given above; or (b) hydrogenating a Schiff's base of Formula IV

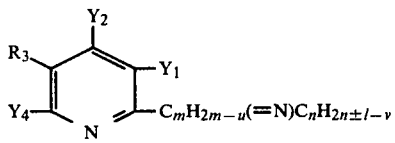

(IV)

wherein one of u and v is the integer 1 and the other is 0, one of $Y_1$, $Y_2$ and $Y_4$ is hydroxy, or the acyloxy radical of an aliphatic or aromatic carboxylic or sulfonic acid, and the others are hydrogen or lower alkyl, and the other symbols have the meaning given above, and hydrolyzing or alcoholyzing any resulting Y-ester; or (c) condensing a primary amine of Formula V

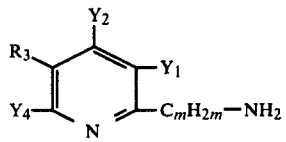

(V)

wherein the symbols have the above meaning, with a reactive ester of the alcohol $C_nH_{2n\pm1}$—OH in the presence of a strong base, and hydrolyzing or alcoholyzing any resulting Y-ester; or (d) reducing an amide of Formula VI

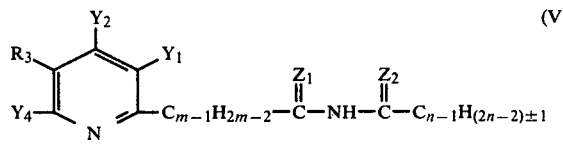

(VI)

wherein one of $Z_1$ and $Z_2$ represents oxo and the other two hydrogen atoms, and the other symbols have the above meaning, with a simple or complex light metal hydride, and hydrolyzing or alcoholyzing any resulting Y-ester and, if desired, converting any resulting compound into another compound of the invention.

Said metallic substituent $X_1$, $X_2$ or $X_4$ in compounds III contains preferably lithium, sodium or halomagnesium, whereas said acyl radicals are advantageously lower alkanoyl or alkanesulfonyl, unsubstituted or lower alkylated, alkoxylated and/or halogenated benzoyl, benzenesulfonyl or carbobenzyloxy, such as acetyl, propionyl, methanesulfonyl, benzoyl, p-toluyl, p-anisoyl, m-chlorobenzoyl, benzenesulfonyl, tosyl or carbobenzyloxy.

The hydrolysis of said compounds III is advantageously performed with water or, depending on the metallic or nonmetallic character of X, with diluted inorganic or organic acids or bases respectively, e.g., aqueous alkalies or acids, e.g., those listed below, preferably at or below room temperature, such as at about 0°, in case the X-substituents are metallic, or above room temperature, such as 40°–120°, in case they are nonmetallic. Said carbobenzyloxy compounds III may also be cleaved hydrogenolytically, as known per se in peptide-synthesis, i.e., with hydrogen in the presence of noble metal catalysts, e.g., palladium or platinum.

The metallic starting material III can be prepared by condensing compounds of the formulae

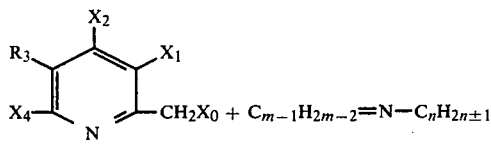

wherein $X_0$ is an alkali metal or alkaline earth metal halide, and all other symbols have the meaning given above, under anhydrous conditions, advantageously in polar diluents, such as open or cyclic ethers, e.g., diethyl ether or tetrahydrofuran, and at temperatures below room temperature, e.g., between about 10° and −20°. Alternatively, said acyl derivatives III are prepared by condensing compounds of the formula

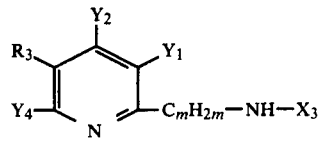

wherein $X_3$ is said acyl radical of an aliphatic or aromatic carboxylic or sulfonic acid, with a reactive ester of the alcohol $C_nH_{2n\pm1}OH$, mentioned below.

The Schiff's bases IV are conventionally hydrogenated, either with catalytically activated or nascent hydrogen, such as hydrogen in the presence of palladium, platinum or nickel catalysts, or generated electrolytically; or with simple or complex light metal hydrides, e.g., boranes, alane, or alkali metal boro- or cyanoborohydrides, such as sodium borohydride or cyanoborohydride. Any resulting Y-ester may be hydrolyzed or alcoholyzed in known manner, advantageously with the use of strong inorganic bases, e.g., aqueous alkali metal hydroxides or carbonates; or lower alkanols respectively.

The starting material IV is conveniently obtained by condensing compounds of the formulae

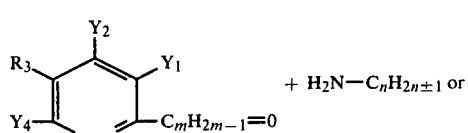

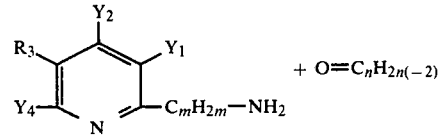

and the aldehydic or ketonic pyridine precursors thereof are similarly obtained as the compounds III, i.e., by condensing said hydroxypicoline metal salts with corresponding alkanoic acid amides or nitriles, e.g., formamide, dimethylacetamide or propionitrile, and hydrolyzing the condensate with water or diluted acids, or hydrogenating it to said amines. The latter may also be obtained from said aldehydes or ketones by converting them conventionally into their oximes, and reducing them with catalytically activated hydrogen, preferably with the use of rhodium on alumina. If desired, the resulting hydroxypyridines may be esterified, for example with the use of lower alkanoic, alkanesulfonyl, benzoic, benzenesulfonyl or benzyloxyformyl halides.

The primary amines V are preferably condensed with said esters derived from strong inorganic acids, such as hydrohalic, e.g., hydrochloric, hydrobromic or advantageously hydriodic acid, or the organic sulfonic acids mentioned above. Said strong bases utilized are preferably tertiary amines, such as tri-lower alkylamines, e.g., di-isopropyl-ethylamine, or cyclic nitrogen bases, such as pyridine or lutidine. Care should be taken to avoid a simultaneous quaternization of the resulting secondary amines I, e.g., by avoiding excessive amounts of said reactive esters and/or temperatures excessively above room temperature. The preparation of said compounds V has been described above.

The reduction of the amides VI is conventionally carried out with the stronger light metal hydrides mentioned for said Schiff's bases IV, advantageously alane in solution of said strong bases, or alkali metal aluminum hydride, e.g., lithium aluminumhydride, lithium or sodium tri-lower alkoxy or bis-alkoxyalkoxy aluminumhydrides, e.g., lithium tri-t-butoxy-aluminumhydride or sodium bis-(2-methoxyethoxy)-aluminumhydride.

The starting material VI is conventionally obtained from said primary amines V and corresponding halides or anhydrides of the acids $C_{n-1}H_{(2n-2)\pm1}COOH$; or from hydroxypyridyl-2-alkanoic acid halides or anhydrides and the amines $H_2N-C_nH_{2n\pm1}$.

The compounds of the invention so obtained can be converted into each other according to known methods. For example, resulting unsaturated compounds I with $C_nH_{2n-1}$ being lower alkenyl, may be catalytically hydrogenated, e.g., as mentioned for compounds IV. Any resulting free compound can be converted into a corresponding acid addition salt, for example, by reacting it with an inorganic or organic acid, preferably a pharmaceutically acceptable carboxylic or sulfonic acid, or with a corresponding anion exchange preparation, and isolating the desired salt. An acid addition salt may be converted into the free compound by treatment with a base, e.g., a metal hydroxide, ammonia or a hydroxyl ion exchange preparation. Pharmaceutically acceptable acids are, for example, inorganic acids, such as hydrohalic, e.g., hydrochloric, hydrobromic, sulfuric, phosphoric, nitric or perchloric acid, or organic acids, e.g., aliphatic or aromatic carboxylic or sulfonic acids, such as formic, acetic, propionic, succinic, glycollic, lactic, malic, tartaric, citric, ascorbic, maleic, hydroxymaleic, pyroracemic, phenylacetic, benzoic, 4-aminobenzoic, anthranilic, 4-hydroxybenzoic, salicylic, pamoic, nicotinic, methanesulfonic, ethanesulfonic, hydroxyethanesulfonic, ethylenesulfonic, benzenesulfonic, halobenzenesulfonic, toluenesulfonic, naphthalenesulfonic, sulfanilic or cyclohexylsulfamic acid.

These or other salts, for example, the picrates, can also be used for purification of the bases obtained; the bases are converted into salts, the salts are separated and the bases are liberated from the salts. In view of the close relationship between the free compounds and the compounds in the form of their salts, whenever a compound is referred to in this context, a corresponding salt is also intended, provided such is possible or appropriate under the circumstances.

Resulting mixtures of isomers can be separated into the single isomers by methods in themselves known, e.g., by fractional distillation, crystallization and/or chromatography. Racemic products can likewise be resolved into the optical antipodes, for example, by separation of diastereomeric salts thereof, e.g., by the fractional crystallization of d- or l-camphor sulfonates or madelates, advantageously those of said Y-esters.

The above reactions are carried out according to standard methods, in the presence or absence of diluents, preferably such as are inert to the reagents and are solvents thereof, of catalysts, condensing or neutralizing agents and/or inert atmospheres, at low temperatures, room temperature or elevated temperatures, at atmospheric or superatmospheric pressure.

The invention also comprises any modification of the above processes, wherein a compound resulting as an intermediate at any stage thereof, is used as starting material and the remaining steps are carried out, or the process is discontinued at any stage thereof, or in which the starting material is formed under the reaction conditions or is used in the form of its salt or reactive derivatives. For example, in the above-described hydrogenation of compounds IV, or optical resolution, said Y-esters will increase the basicity of the secondary amine, but may hydrolyze under basic reaction, e.g., reduction conditions. Analogously, catalytic hydrogenations of carbobenzoxy compounds III, or Schiff's bases IV with an olefinic $C_nH_{2n-1}$ radical will yield the corresponding saturated $C_nH_{2n+1}$ compounds I. In the process of the invention, those starting materials are advantageously selected which yield the above described preferred embodiments thereof, especially those corresponding to Formula II.

The pharmacologically active compounds of the invention are useful in the manufacture of pharmaceutical compositions comprising an effective amount thereof in conjunction or admixture with excipients suitable for either enteral or parenteral administration. Preferred are tablets and gelatin capsules comprising the active ingredient together with (a) diluents, e.g., lactose, dextrose, sucrose, mannitol, sorbitol, cellulose and/or glycine, (b) lubricants, e.g., silica, talcum, stearic acid, its magnesium or calcium salt and/or polyethyleneglycol, for tablets also (c) binders, e.g., magnesium aluminum silicate, starch paste, gelatin, tragacanth, methylcellulose, sodium carboxymethylcellulose and/or polyvinylpyrrolidone, if desired, (b) disintegrants, e.g., starches, agar, alginic acid or its salts, enzymes of the binders or effervescent mixtures and/or (e) adsorbents, colorants, flavors and sweeteners. Injectable compositions are preferably aqueous isotonic solutions or suspensions, and suppositories are advantageously solid fatty emulsions or suspensions. They may be sterilized and/or contain adjuvants, such as preserving, stabilizing, wetting or emulsifying agents, solution promoters, salts for regulating the osmotic pressure and/or buffers. They may also contain other therapeutically valuable substances. Said pharmaceutical compositions are prepared according to conventional mixing, granulating and/or coating methods respectively, and contain about 1 to 75%, preferably 10 to 50%, of the active ingredient.

The following examples, illustrating the invention, are not to be construed as being limitations thereon. Temperatures are given in degrees Centigrade, all parts wherever given are parts by weight and, if not otherwise stated, all evaporations are carried out under reduced pressure, e.g., between 0.1 and 15 mmHg.

EXAMPLE 1

To the solution of 10.9 g of 2-methyl-6-hydroxypyridine in 400 ml of tetrahydrofuran, 88 ml of 2.5 molar n-butyllithium in hexane are added dropwise while stirring under nitrogen at 0°. After 2 hours 10.2 g of 1-isopropyliminoethane are added rapidly and the mixture stirred for 2 hours at 0°. It is poured into 200 ml of saturated aqueous ammonium chloride, the organic layer separated and the aqueous solution extracted 4 times with 150 ml of methylene chloride. The combined organic solutions are dried, filtered, evaporated and the residue is chromatographed on 300 g of silica gel with methanoldiethyl ether (5:1) as moving phase. The eluate is evaporated, the residue taken up in ethanol, neutralized with ethanolic fumaric acid and the resulting precipitate recrystallized from ethanol, to yield the monofumarate of N-[2-(6-hydroxy-2-pyridyl)propyl]-isopropylamine of Formula II, with R=OH, R'=H and $C_pH_{2p\pm 1}=CH(CH_3)_2$, melting at 193.5°–194°.

The starting material is freshly prepared as follows: To 112.5 ml of redistilled acetaldehyde, cooled to −20° to −30°, 170.3 ml of isopropylamine are added dropwise while stirring at said temperature. The mixture is stirred for 90 minutes at 0°, whereupon 50 g of potassium hydroxide pellets are added. The mixture is allowed to stand in the cold and decanted off the liquified base. Another 50 g of potassium hydroxide pellets are added twice more and the mixture finally allowed to stand overnight in the refrigerator. The supernatant product is separated, distilled and the fraction boiling at 59°–62° at atmospheric pressure collected, to yield the isopropyliminoethane.

EXAMPLE 2

To the solution of 10.9 g of 2-methyl-3-hydroxypyridine in 400 ml of tetrahydrofuran, 88 ml of 2.5 molar n-butyllithium in hexane are added dropwise while stirring under nitrogen and keeping the temperature at about 0°. Stirring is continued for 2 hours at 0°–5°, whereupon 0.2 g of isopropyliminoethane are added rapidly and the temperature is maintained at 0°–5°. After stirring the resulting mixture 2 more hours at said temperature, it is poured into 200 ml of saturated aqueous ammonium chloride. The organic layer is separated, evaporated, redissolved in 100 ml of water and the solution extracted 5 times with 50 ml of diethyl ether. The aqueous phase is saturated with sodium chloride, extracted 5 times with 200 ml of methylene chloride, the combined extracts dried, filtered and evaporated. The residue is dissolved in ethanol and the solution neutralized with ethanolic fumaric acid. The resulting suspension is filtered and the residue recrystallized from ethanol, to yield the hemi-fumarate of N-[2-(3-hydroxy-2-pyridyl)propyl]-isopropylamine of Formula II, with R=H, R'=OH and $C_pH_{2p\pm 1}=CH(CH_3)_2$, melting at 199°–199.5°.

EXAMPLE 3

Preparation of 10,000 tablets, each containing 100 mg of the active ingredient:

| Formula: | |
|---|---|
| N-[2-(6-hydroxy-2-pyridyl)propyl]-isopropylamine fumarate | 1,000.00 g |
| Lactose | 2,535.00 g |
| Corn starch | 125.00 g |
| Polyethylene glycol 6,000 | 150.00 g |
| Talcum powder | 150.00 g |
| Magnesium stearate | 40.00 g |
| Purified water | q.s. |

PROCEDURE

All powders are passed through a screen with openings of 0.6 mm. Then the drug substance, lactose, talcum, magnesium stearate and half of the starch are mixed in a suitable mixer. The other half of the starch is suspended in 65 ml of water and the suspension added to the boiling solution of the polyethylene glycol in 260 ml of water. The paste formed is added to the powders, which are granulated, if necessary, with an additional amount of water. The granulate is dried overnight at 35°, broken on a screen with 1.2 mm openings and compressed into tablets using concave punches with 10.3 mm diameter, uppers bisected.

EXAMPLE 4

Preparation of 1,000 capsules each containing 50 mg of the active ingredient:

| Formula: | |
|---|---|
| N-[2-(3-hydroxy-2-pyridyl)propyl]-isopropylamine fumarate | 50.00 g |
| Modified corn starch | 5.00 g |
| Lactose | 143.75 g |
| Magnesium stearate | 1.00 g |
| Surfactant | 0.25 g |

PROCEDURE

All the powders are passed through a screen with openings of 0.6 mm. Then the drug substance is mixed first with the magnesium stearate and surfactant, whereupon the starch and lactose are added and mixed until homogeneous. No. 2 capsules are filled with 200 mg each, using a filling machine.

What is claimed is:

1. A secondary hydroxypyridylalkylamine of the formula

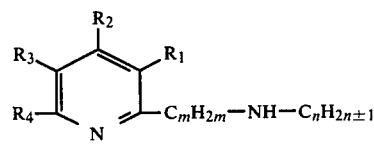

wherein one of $R_1$, $R_2$ and $R_4$ is hydroxy, and the others, as well as $R_3$, are hydrogen or lower alkyl; m is an integer from 2 to 4; and n is an integer from 1 to 7; or a pharmaceutically acceptable acid addition salt thereof.

2. A compound as claimed in claim 1, in which formula one of $R_1$, $R_2$ and $R_4$ is hydroxy, and the others, as well as $R_3$, are hydrogen or methyl, m is the integer 2 or 3; and n is an integer from 2 to 6; or a pharmaceutically acceptable acid addition salt thereof.

3. A compound as claimed in claim 1 and corresponding to the formula

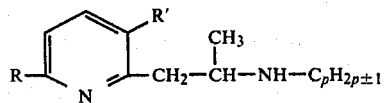

wherein one of R and R' is hydroxy and the other is hydrogen; and p is an integer from 3 to 6; or a pharmaceutically acceptable acid addition salt thereof.

4. A compound as claimed in claim 3, in which formula $C_pH_{2p\pm1}$ represents i-propyl, t-butyl, allyl or cyclopropyl; or a pharmaceutically acceptable acid addition salt thereof.

5. A compound as claimed in claim 4 and being the N-[2-(3-hydroxy-2-pyridyl)propyl]-isopropylamine, or a pharmaceutically acceptable acid addition salt thereof.

6. A compound as claimed in claim 4, and being the N-[2-(6-hydroxy-2-pyridyl)propyl]-isopropylamine, or a pharmaceutically acceptable acid addition salt thereof.

7. A cardioprotective pharmaceutical composition comprising an effective amount of a compound claimed in claim 1, together with an inert pharmaceutical excipient.

8. A method of alleviating cardiac ischemia in mammals, which consists in administering to them enterally or parenterally a cardioprotective amount of a composition as claimed in claim 7.

* * * * *